(12) United States Patent
Ishikawa et al.

(10) Patent No.: US 7,847,132 B2
(45) Date of Patent: Dec. 7, 2010

(54) HEPATIC FIBROSIS INHIBITOR

(75) Inventors: Naohisa Ishikawa, Aichi-gun (JP);
Satoru Sugiyama, Nagoya (JP);
Tokutaro Miki, Hachioji (JP); Hiroshi Nishikawa, Shizuoka (JP)

(73) Assignee: Nippon Hypox Laboratories Incorporated, Tokyo (JP)

( * ) Notice: Subject to any disclaimer, the term of this patent is extended or adjusted under 35 U.S.C. 154(b) by 0 days.

(21) Appl. No.: 12/591,982

(22) Filed: Dec. 7, 2009

(65) Prior Publication Data

US 2010/0184858 A1 Jul. 22, 2010

Related U.S. Application Data

(62) Division of application No. 12/385,603, filed on Apr. 14, 2009, now abandoned.

(30) Foreign Application Priority Data

Apr. 14, 2008 (JP) .............................. 2008-105101

(51) Int. Cl.
*C07C 409/00* (2006.01)
*A61K 31/045* (2006.01)

(52) U.S. Cl. .................. 568/560; 514/724; 514/730

(58) Field of Classification Search ................ 568/560; 514/724, 730
See application file for complete search history.

(56) References Cited

FOREIGN PATENT DOCUMENTS

| JP | 5-301836 | 11/1993 |
|----|----------|---------|
| JP | 6-100441 | 4/1994 |
| JP | 8-67627 | 3/1996 |
| JP | 2002-241366 | 8/2002 |
| JP | 2004-352661 | 12/2004 |
| JP | 2005-41837 | 2/2005 |
| JP | 2005-343889 | 12/2005 |
| JP | 2007-186519 | 7/2007 |
| WO | 00/31135 | 6/2000 |

OTHER PUBLICATIONS

Jian Wu et al., "Hepatic stellate cells: a target for the treatment of liver fibrosis", Journal of Gastroenterology, vol. 35, No. 9, pp. 665-672, 2000.
Tadayuki Hino et al., "HTHQ (1-0-hexyl-2,3,5-trimethylhydroquinone), an anti-lipid-peroxidative compound: its chemical and biochemical characterizations", Biochimica et. Biophysica Acta, 1425, pp. 47-60, Sep. 16, 1998.
Communication dated Feb. 24, 2010 issued in connection with the European application corresponding to the present U.S. application.
European Search Report dated Sep. 4, 2009 issued in corresponding European Application No. 09 15 7413.
Giuseppe Poli, "Pathogenesis of liver fibrosis: role of oxidative stress", Molecular Aspects of Medicine, 21, pp. 49-98, XP-002540587, 2000.
Kuniharu et al., Akita, "Inhibiting Hepatic Fibrosis Against Cirrhosis", Jpn J Med Pharma Sci (Igaku to Yakugaku), Japan, May 2001, vol. 45-5, pp. 720-728.
Fujii et al., Hideki, "Molecular Mechanism of Hepatic Fibrosis—Mainly Stellate Cell", Weekly Journal of Clinical and Experimental Medicine (Igaky no Ayumi), Japan, 2006, pp. 198-202.

*Primary Examiner*—Sikarl A Witherspoon
(74) *Attorney, Agent, or Firm*—Wenderoth, Lind & Ponack, L.L.P.

(57) ABSTRACT

The progression of hepatic fibrosis and hepatic cirrhosis caused by various hepatic disorders and damages such as chronic hepatitis can be restrained by hepatic fibrosis inhibitor containing a compound represented by the following chemical formula:

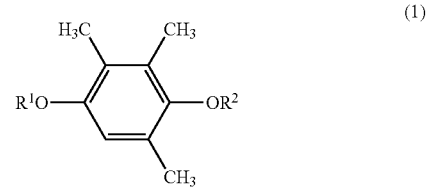

(1)

wherein, R1 represents an alkyl group with a carbon number of 4 to 8, and R2 represents a hydrogen atom, alkylcarbonyl group with a carbon number of 2 to 6, or alkoxycarbonyl group with a carbon number of 2 to 6.

2 Claims, 8 Drawing Sheets

HEPATIC FIBROSIS INHIBITOR

This application is a Divisional application of Ser. No. 12/385,603, filed Apr. 14, 2009 now abandoned.

BACKGROUND OF THE INVENTION

1. Field of the Invention

This invention relates to a hepatic fibrosis inhibitor.

2. Description of the Related Art

Hepatic fibrosis is a condition in which production of fibrous tissues referred to as extracellular matrix formed of collagen and complex carbohydrate is accelerated, consequently to be gradually accumulated with progression of inflammation in the course of repairing necrotic hepatocytes necrotized by viral hepatitis, alcohol liver diseases, autoimmune hepatic disorders, metabolic hepatic disorders or the like.

In early stages of inflammation, the hyperplastic extracellular matrix is eventually absorbed and cured without being accumulated, but production of the matrix in a case of chronic hepatitis maintaining its inflammatory conditions exceeds decomposition and absorption of the matrix to continue accumulation of the fibrous tissues, consequently to repeat a vicious circle that the hepatic parenchymal cells pressured by the accumulated fibrous tissues are damaged, resulting in accelerated production of the fibrous tissues, and eventually lead to hepatic cirrhosis in which the liver becomes hardened and malfunctions due to the fibrous tissues.

The hepatic cirrhosis is difficult to cure, and, in many cases, the liver cirrhosis progresses to liver cancer. Particularly, hepatitis C which is possibly spread to others by virus-tainted blood products and has become a serious social issue progresses from chronic hepatitis to the liver cancer via the hepatic cirrhosis at high rates. Hence, treatment to suppress the hepatic inflammation and fibrosis is important, but at present, there is a paucity of therapeutic drugs having few side-effects and high curative effect.

Recently, it has been thought that hepatic stellate cells and TGF-β undertake an important role in progression of hepatic fibrosis. The hepatic stellate cells are activated by cytokine released by the inflammatory cells such as macrophages to actively produce the extracellular matrix including type I collagen. Meanwhile, TGF-β was identified as a cytokine for stimulating genetic transformation and proliferation of normal fibroblasts and has effects for stimulating the proliferation of the activated stellate cells and the production of the extracellular matrix and antiproliferative activity of the hepatic parenchymal cells. Thus, the development of curative drugs for suppressing the effect of TGF-β or excess production of TGF-β has been advanced in order for controlling the hepatic fibrosis.

Based on this viewpoint, as examples of an inhibitor for inhibiting hepatic fibrosis due to an anti-TGF-β action or TGF-β production inhibiting action, there have been studied an integrin inactivator in Patent Literature 1, an ALK5 inhibitor in Patent Literature 2, and an anti-TGF-β receptor peptide in Patent Literature 3. Further, as one example, Patent Literature 4 discloses that an iNOS-activity inhibitor of a specific configuration having an action of inhibiting NO-production shows suppressant actions on the production of TGF-β and hepatic fibrosis.

A hydroquinone derivative represented by the following chemical formula (1) has potent antioxidant action and NO-production inhibiting action. The inventors of the present invention have devised an antioxidant agent containing such a compound as an active constituent (Patent Literature 5), a curative drug for refractory inflammatory affection such as arthritis rheumatoides and nonspecific imflammatory bowel diseases (Patent Literature 6), a carcinogenic inhibitor (Patent Literature 7), and a therapeutic agent for arterial sclerosis (Patent Literature 8).

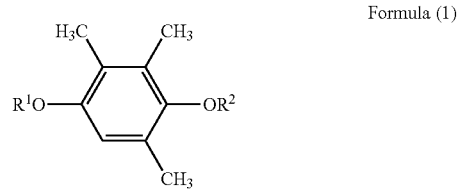

Formula (1)

Patent Literature 9 provided by the inventors of the present invention discloses a therapeutic composition for treatment of liver disorder containing the present compound as an active constituent. This literature concretely describes with respect to the effectiveness of the composition against alpha-naphthyl isothiocyanate (ANIT)-induced acute hepatic damage in mice on the basis of pharmacological examples and clarifies high safety of the composition through safety testing.

Patent Literature 1: Japanese Published Unexamined Pub. No. 2002-530431

Patent Literature 2: Japanese Published Unexamined Appln. No. 2005-343889

Patent Literature 3: Japanese Published Unexamined Appln. No. 2007-186519

Patent Literature 4: Japanese Published Unexamined Appln. No. 2005-41837

Patent Literature 5: Japanese Published Unexamined Appln. HEI 5-301836

Patent Literature 6: Japanese Published Unexamined Appln. No. 2004-352661

Patent Literature 7: Japanese Published Unexamined Appln. HEI 6-100441

Patent Literature 8: Japanese Published Unexamined Appln. No. 2002-241366

Patent Literature 9: Japanese Published Unexamined Appln. HEI 8-67627

However, each of the compounds mentioned in Patent Literatures 1-4 is still being studied as a hepatic fibrosis inhibitor. There has not yet been found an effective drug for restraining the progression of hepatic fibrosis and hepatic cirrhosis. Also, Patent Literatures 5-9 do not mention that the compound represented by the aforementioned chemical formula (1) exerts a suppressant action for suppressing hepatic fibrosis.

In the meantime, the inventors of this invention have found that the antibody valency of Naofen (GenBank Accession Number EF613262) which is in vivo protein newly found as an anti-verotoxin 2 (VT2) antibody reactive substance increases in an induction model of hepatic cirrhosis and hepatic fibrosis caused by carbon tetrachloride in rats. In the light of the fact that the increase of the antibody valency occurs previous to the production of TGF-β1 and the production of collagen, it has been found that the Naofen affects the hepatic cirrhosis and hepatic fibrosis earlier than the production of TGF-β1.

Hence, the inventors of this invention have earnestly carried their investigation forward to find a substance with suppressive activity for suppressing the increase of antibody valency of intrahepatic Naofen in the aforementioned model as a substance having a suppressant action on hepatic fibrosis. Further, the inventors have continued the research in anticipation of the suppressant action of Naofen on the ground that the hydroquinone derivative represented by the foregoing general formula (1) has the suppressant action on hepatic damage.

In the meanwhile, the causal relation among the hepatic fibrosis, the production of TGF-β1 and inducible NO synthase enzyme-derived NO has not yet fully manifested, and also, it is not clarified whether the NO-production inhibiting action works as the suppressant action on hepatic fibrosis as well. The inventors of this invention have further pursued the research for demonstrating the prediction about the hydroquinone derivative represented by the aforementioned chemical formula (1) has the TGF-β production inhibiting action as well as the iNOS-activity inhibitor and the suppressant action on hepatic fibrosis.

As a result, the present invention has been achieved by finding that the aforementioned compound which has effects for inhibiting the expression of Naofen and further the expression of TGF-β1 mRNA, thus to inhibit hepatic fibrosis is useful as an inhibitor for suppressing hepatic fibrosis.

SUMMARY OF THE INVENTION

In view of the foregoing disadvantages inherent in the known types of hepatic fibrosis inhibitors now present in this field, the present invention provides a hepatic fibrosis inhibitor comprising, as an effective ingredient, hydroquinone derivative containing a compound represented by Formula (2):

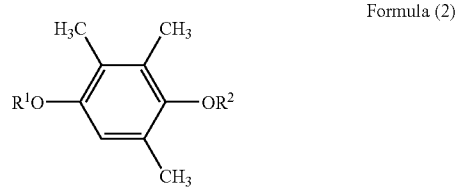

Formula (2)

wherein, R1 represents an alkyl group with a carbon number of 4 to 8, and R2 represents a hydrogen atom, alkylcarbonyl group with a carbon number of 2 to 6, or alkoxycarbonyl group with a carbon number of 2 to 6.

Such compounds as described above serve to inhibit the expression of a substance participating in hepatic fibrosis prior to TGF-β1, i.e. expression of Naofen. The mechanism of the compounds for inhibiting the expression of Naofen has not yet been clear, but the inventors of this invention predict that the suppression of Naofen is carried out by a mechanism mediating the suppressant action of IκB kinase, which resembles the NO-production inhibiting action effected through a mechanism of suppressing phosphorylation of IκB of the hydroquinone derivative. The compounds further exhibit the NO-production inhibiting action to suppress the production of TGF-β to stimulate the hepatic fibrosis similarly to the iNOS-activity inhibitor. These actions serve to control the collagen production in the fibrotic liver, thus to constrict the accumulation of fibrous tissue and suppress the fibrosis.

The present invention further provides a hepatic fibrosis inhibitor in which the compound represented by the aforementioned chemical formula (2) is 2,3,5-trimethyl hydroquinone-1-hexylether or 2,3,5-trimethyl hydroquinone-1-hexylether 4-acetate.

The hydroquinone derivative comprising the compound identified by the chemical formula (2) according to the present invention has a function of inhibiting the expression of Naofen participating in hepatic fibrosis and suppressing the production of TGF-β, so that the fibrosis can be dominantly suppressed. Besides, the hydroquinone derivative of the invention is superior in safety in the liver. Thus, the compound containing the hydroquinone derivative as the active constituent can be effectively used as the hepatic fibrosis inhibitor.

Furthermore, the 2,3,5-trimethyl hydroquinone-1-hexylether and 2,3,5-trimethyl hydroquinone-1-hexylether 4-acetate are superior in terms of pharmacologic activity and biocompatibility, and particularly, can be effectively utilized.

DETAILED DESCRIPTION OF THE PREFERRED EMBODIMENTS OF THE INVENTION

Figure 1:
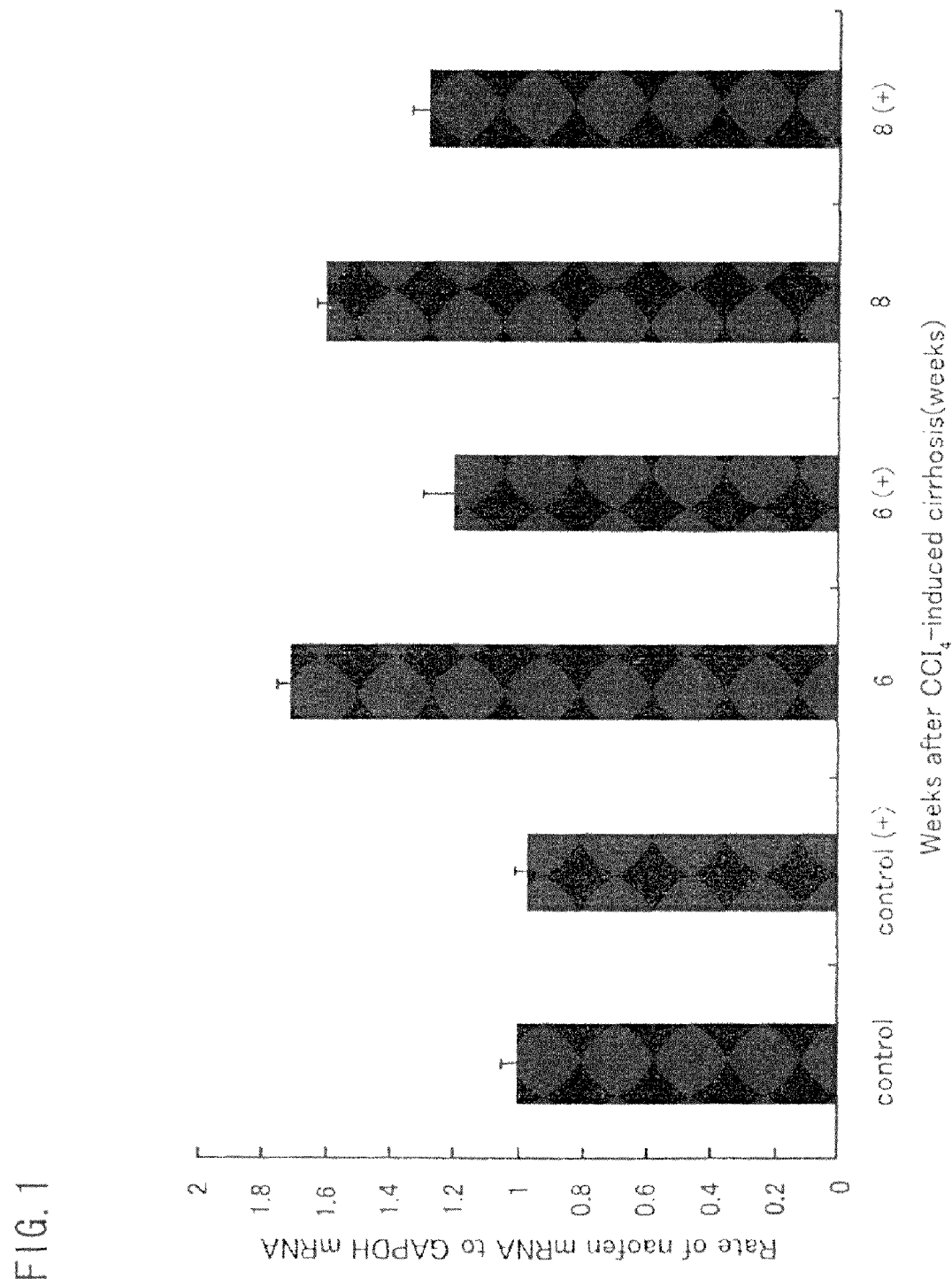
FIG. 1 is a diagram showing the action of the compound 1 relative to an mRNA-expression level of Naofen in the liver.

Hereinafter, a hepatic fibrosis inhibitor according to the present invention will be described in detail.

In the compounds contained in the hepatic fibrosis inhibitor of the invention, which is identified by the chemical formula (2), the alkyl group having the carbon number of 4 to 8, which is expressed by R1 in the formula, may be of a straight-chain, bifurcated or circular structure. As an example, there can be enumerated various butyl groups, pentyl groups, hexyl groups, heptyl groups, octyl groups, cyclobutyl groups, cyclopentyl groups, cyclohexyl groups, cycloheptyl groups, and cyclooctyl groups. The compound formed in a straight-chain having the carbon number of 4-7 is applicative preferably from the aspect of pharmacologic activity and biocompatibility. Specifically, an n-hexyl group is suitable.

The alkylcarbonyl group in R2, which has the carbon number of 2 to 6, may be formed of a straight-chain or bifurcated structure. As an example, there can be enumerated acetyl groups, propionyl groups, butyryl groups and isobutyryl groups. The alkoxycarbonyl group having the carbon number of 2 to 6 in R2 may be formed of a straight-chain or bifurcated structure. As an example, there can be enumerated methoxycarbonyl groups, ethoxycarbonyl groups, propoxycarbonyl groups, and isopropoxycarbonyl groups.

In particular, as examples of the compounds identified by the aforementioned chemical formula (2), which are desirable from the perspective of pharmacologic activity, there may be enumerated 2,3,5-trimethyl hydroquinone-1-butyl ether, 2,3,5-trimethyl hydroquinone-1-hexylether, and 2,3,5-trimethyl hydroquinone-1-hexylether 4-acetate.

The compounds identified by the aforementioned chemical formula (2) can be produced by, for instance, a method described in Patent Literature 5 as mentioned above.

The hepatic fibrosis inhibitor according to the present invention contains the hydroquinone derivative identified by the aforementioned chemical formula (2) as the active constituent and can be prepared into drug products with the addition of pharmaceutically approved additive agents such as pharmaceutical carriers and diluting agents. The preparation of the hepatic fibrosis inhibitor of the invention can be carried out by solving orally-bioavailable preparations suitable for being absorbed through the gastrointestinal tract in the form of tablet pharmaceuticals, granular powder, capsules, or internal medicine, parenterally-administered agents or transdermal agents such as injectable solution, suppository, tape and adhesive skin patch, solid preparations, and fluid preparations, or a solid solvent with a suitable solvent in use, taking circulation and storage stability into account, according to a commonly established practice. Further, to elevate the bioavailability and stability of the compounds of the invention, the hepatic fibrosis inhibitor according to the invention may be prepared by a drug delivery system with a pharmaceutical technique of microencapsulation, pulverization, clathration or the like.

The applied dosage of the hepatic fibrosis inhibitor of the invention cannot categorically be determined because it varies with desired curative effect, administration method, age, body weight and other factors, but the daily parenteral dosage of the hepatic fibrosis inhibitor based on weight is about 0.01 to 100 mg of active constituent, preferably, about 0.05 to 10 mg. The daily peroral dosage is about 0.1 to 300 mg of active constituent, preferably, about 0.5 to 100 mg. The administration is performed 1 to 5 divided doses per day.

Embodiments

Next, the present invention will be described in detail with reference to experimental examples, but the invention is not to be considered limited to the experimental examples.

Action on a Rat Model with Carbon Tetrachloride-Induced Liver Cirrhosis

Experimental Example 1

To six-week-old Wister male rats, 3 mL/kg of olive oil containing 40% of carbon tetrachloride or olive oil only were subcutaneously administered twice per week for eight weeks. On a parallel with the administration of the carbon tetrachloride, potable water in which 2,3,5-trimethyl hydroquinone-1-hexylether (compound 1) of the hydroquinone derivative identified by the aforementioned general chemical formula (1) is dissolved at a concentration of 0.3 mg/mL was given to one group of rats daily. Simultaneously, to another groups of rats, only water was given.

There were adopted four animal groups, i.e. olive oil administration group, olive oil-plus-compound 1 administration group, carbon tetrachloride administration group, and carbon tetrachloride-plus-compound 1 administration group, in the experimental example. Each group consists of ten animals. The animals were slaughtered eight weeks after start of administration of the carbon tetrachloride to carry out an examination. The examination items include ELISA measurement of the serum antibody valency of Naofen and RT-PCR measurement of the mRNA-expression level of Naofen in the liver.

Figure 6:
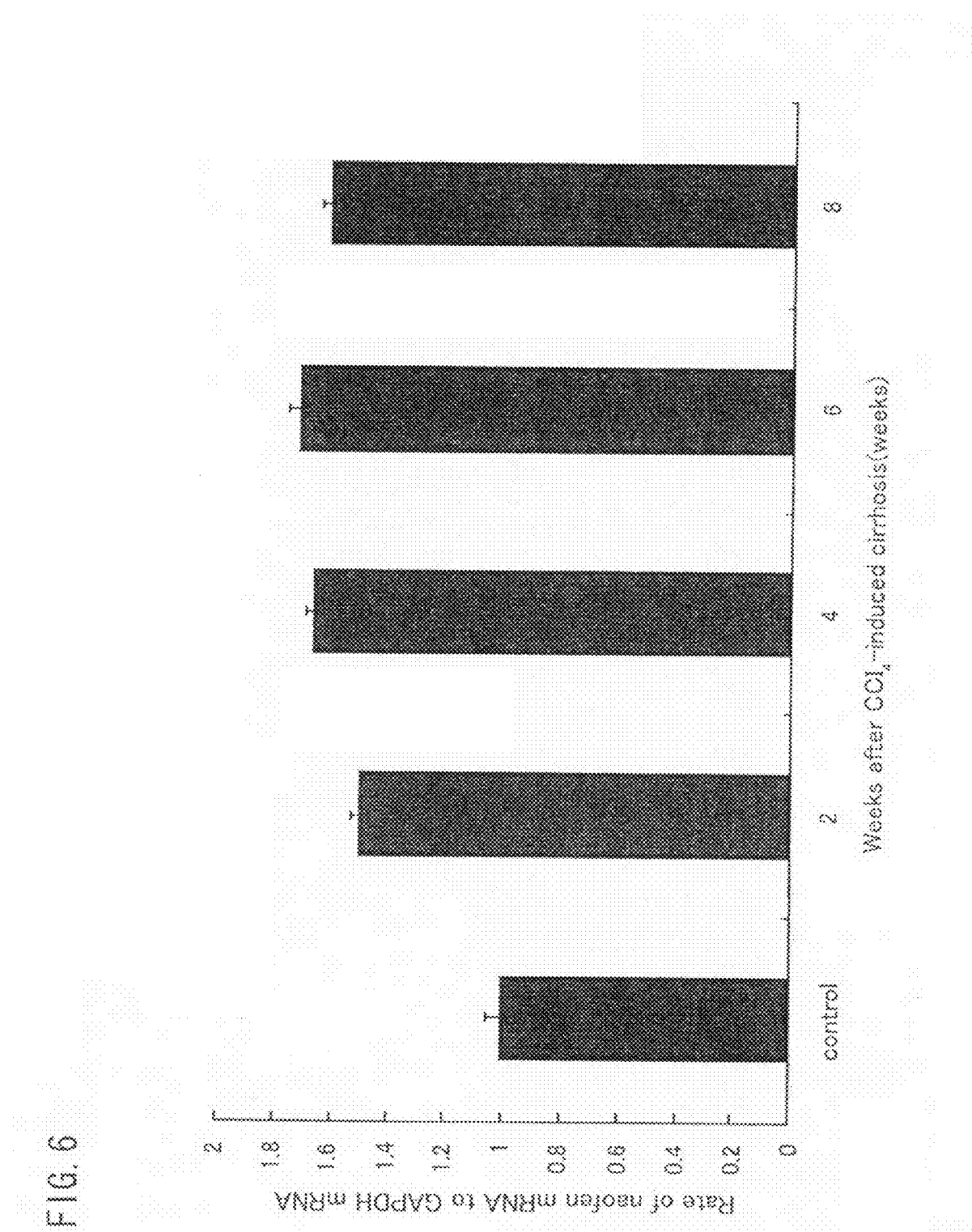
FIG. 6 is a diagram showing the mRNA expression of Naofen in the liver of a rat model with carbon tetrachloride-induced liver cirrhosis.
Figure 7:
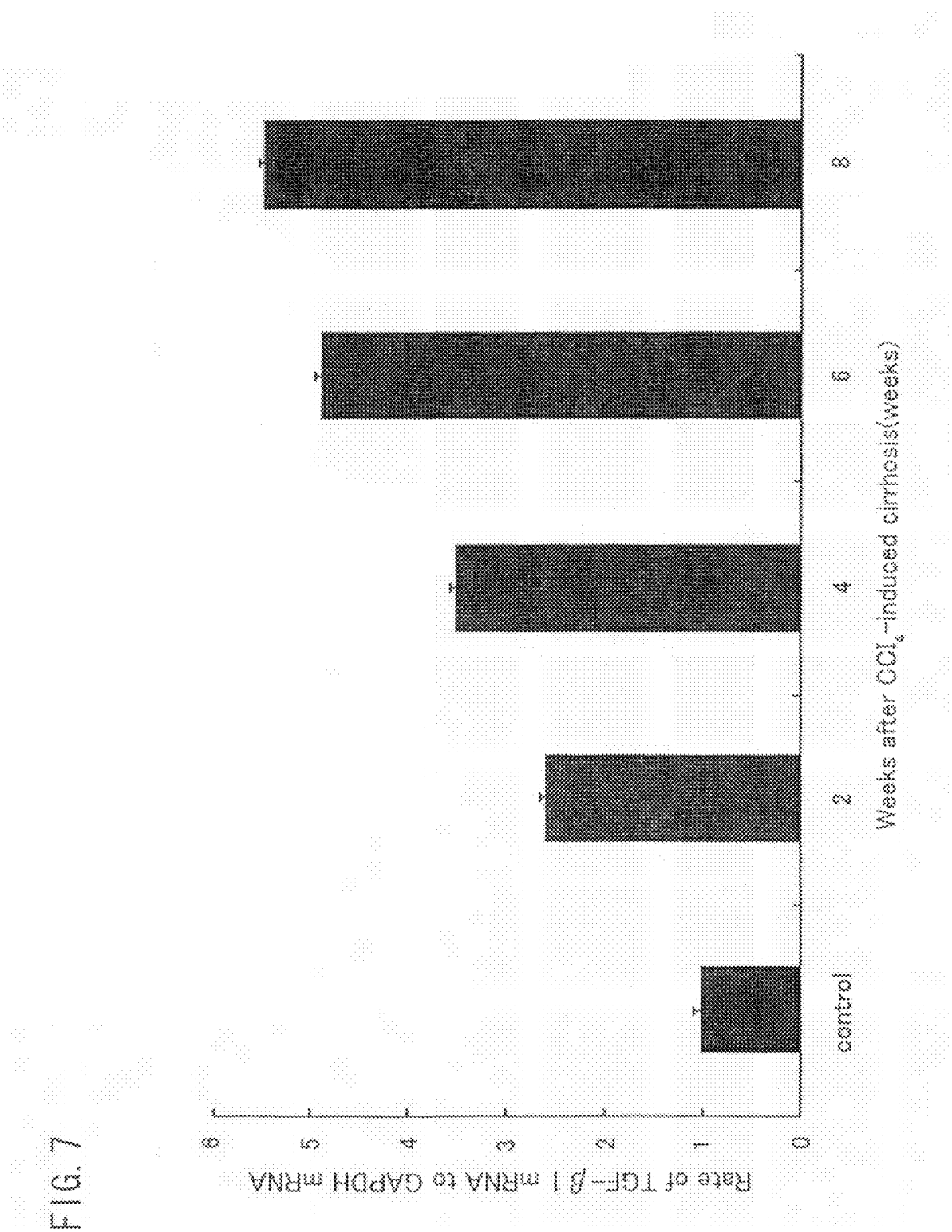
FIG. 7 is a diagram showing the mRNA expression of TGF-β1 in the liver of a rat model with carbon tetrachloride-induced liver cirrhosis.
Figure 8:
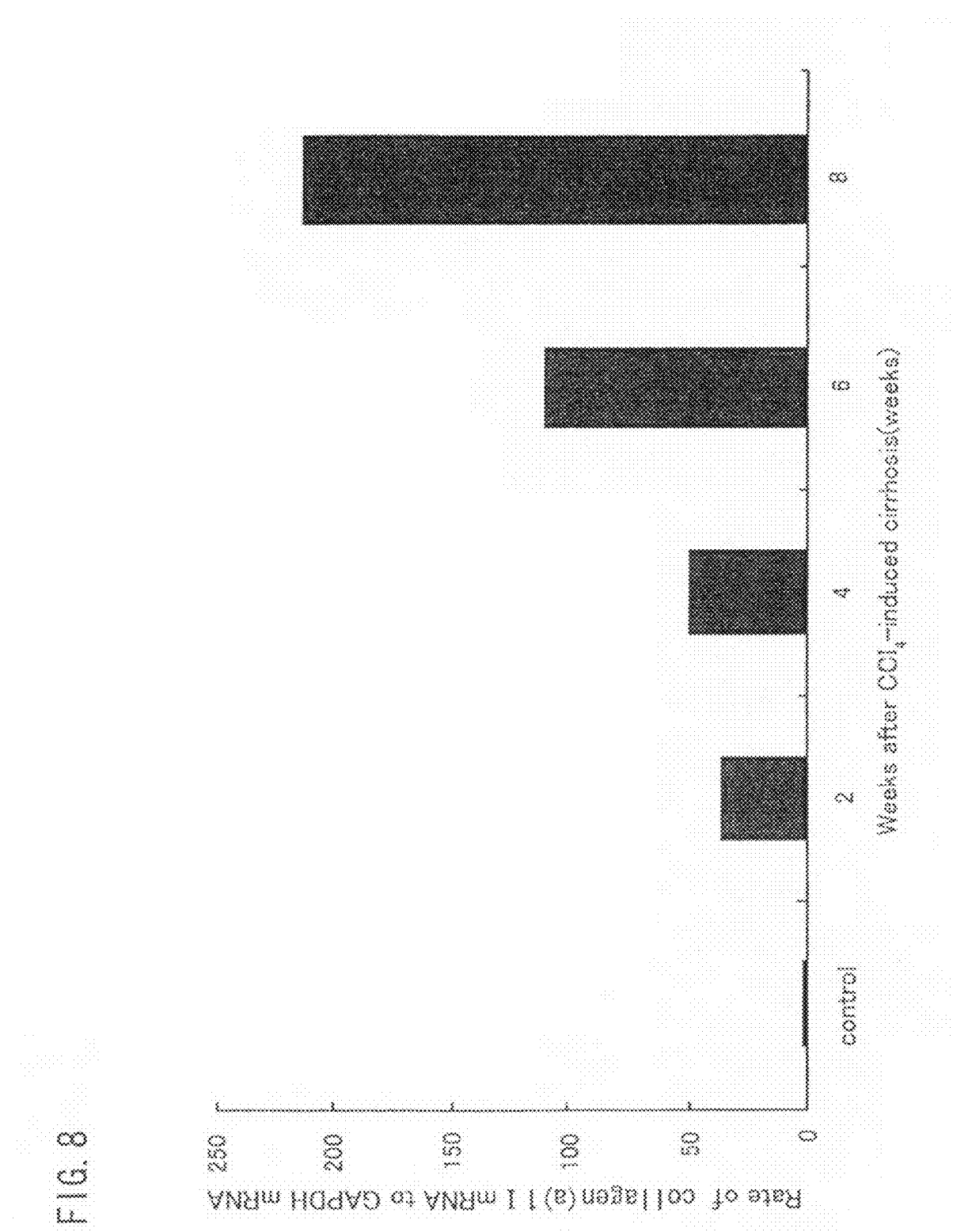
FIG. 8 is a diagram showing the mRNA expression of collagen in the liver of a rat model with carbon tetrachloride-induced liver cirrhosis.

The inventors of this invention have found that, as observed for the mRNA-expression level shown in FIG. 6, the expression of Naofen in the group administered with carbon tetrachloride is remarkably increased in the early stage of cirrhosis progression. The inventors of the invention has further found that the expression of Naofen occurs at a stage earlier than the expression of TGF-$\beta$1 in the progression of hepatic fibrosis on the ground that the expression of Naofen occurs at a stage earlier than the expression of TGF-$\beta$1 shown in FIG. 7 and the expression of intrahepatic collagen shown in FIG. 8.

The mRNA-expression level in this experiment is shown in FIG. 1. It was observed that the increase in expression level of Naofen is suppressed at (weeks 6(+), weeks 8(+)) in the case of administering the compound 1.

Fischer direct probability obtained as the measurement result of the serum antibody valency of Naofen is shown in Table 1. The compound 1 administration group (+) was significantly fewer than the olive oil administration group (−) in antibody valency increase more than 16 times.

TABLE 1

| HX | $V \geq 16$ | $4 < V < 16$ | $V \leq 4$ | Total |
|---|---|---|---|---|
| − | 7 | 0 | 1 | 8 |
| + | 2 | 1 | 4 | 7 |
| Total | 9 | 1 | 5 | 15 |

The experimental results show that the compound 1 exhibits the effect of suppressing the expression level of Naofen, which is increased in cirrhotic and hepatic fibrosis models. That is, the compound 1 has a function of constricting a substance involved in hepatic cirrhosis and hepatic fibrosis in a different manner from TGF-$\beta$1 inhibition cased by NO-production inhibition.

Experimental Example 2

An experimental examination was carried out with a rat model with carbon tetrachloride-induced liver cirrhosis in the same manner as the aforementioned experimental Example 1 except for use of the compound 1 with a concentration of 0.1 mg/mL. The examination includes measurements of some hepatic damage indexes such as blood AST, ALT, albumin (ALB) and total bilirubin (T-Bil), measurement of hyaluronan (HA) concentration serving as a maker of hepatic fibrosis, autopsy finding, measurements of body weight and organ weight, measurements of expression levels of TGF-$\beta$1 mRNA and type-I collagen mRNA in biologic cells by RT-PCR, and a histopathologic inspection.

Figure 2:
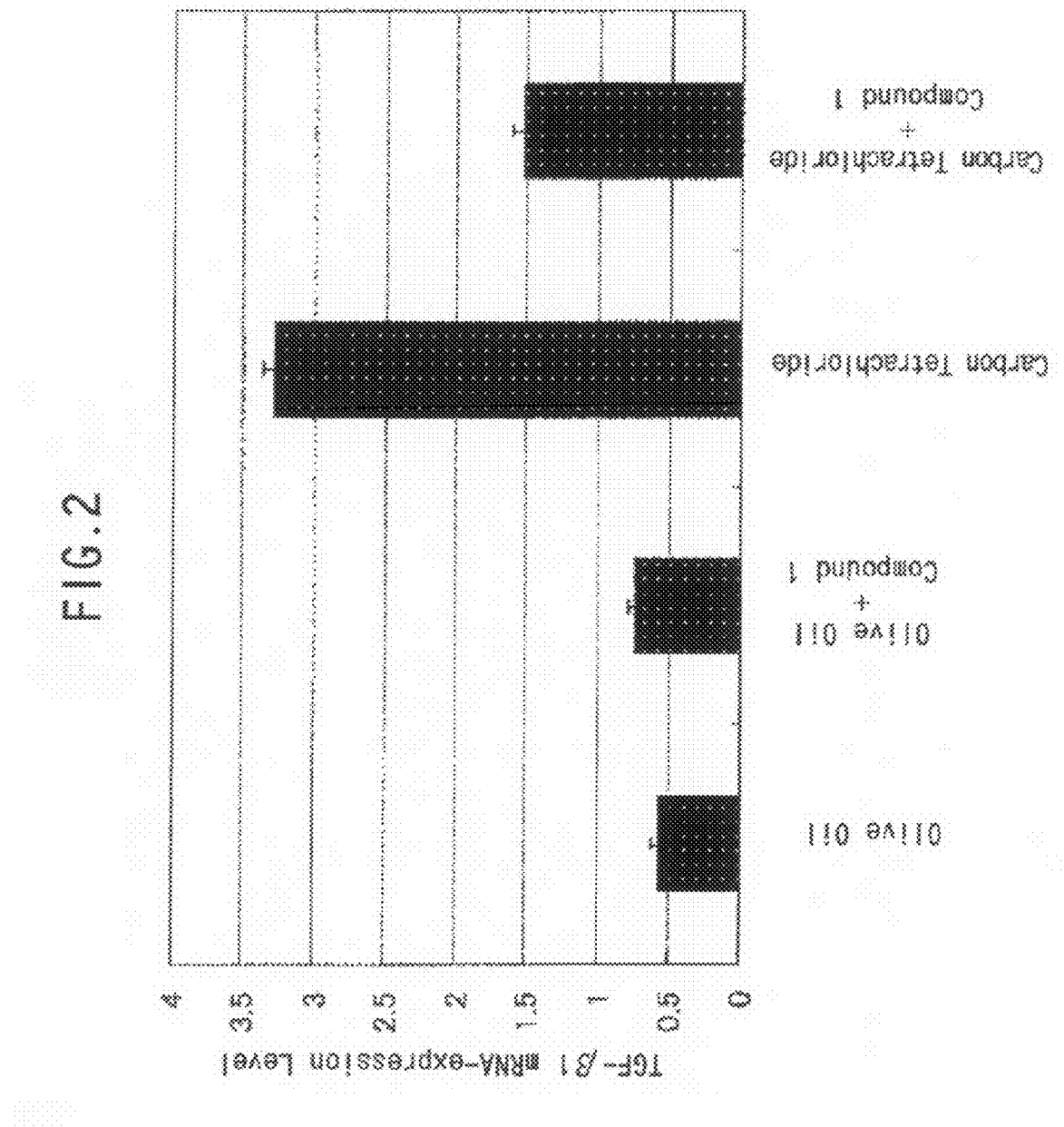
FIG. 2 is a diagram showing the action of the compound 1 relative to a TGF-β1 mRNA-expression level in the liver.
Figure 3:
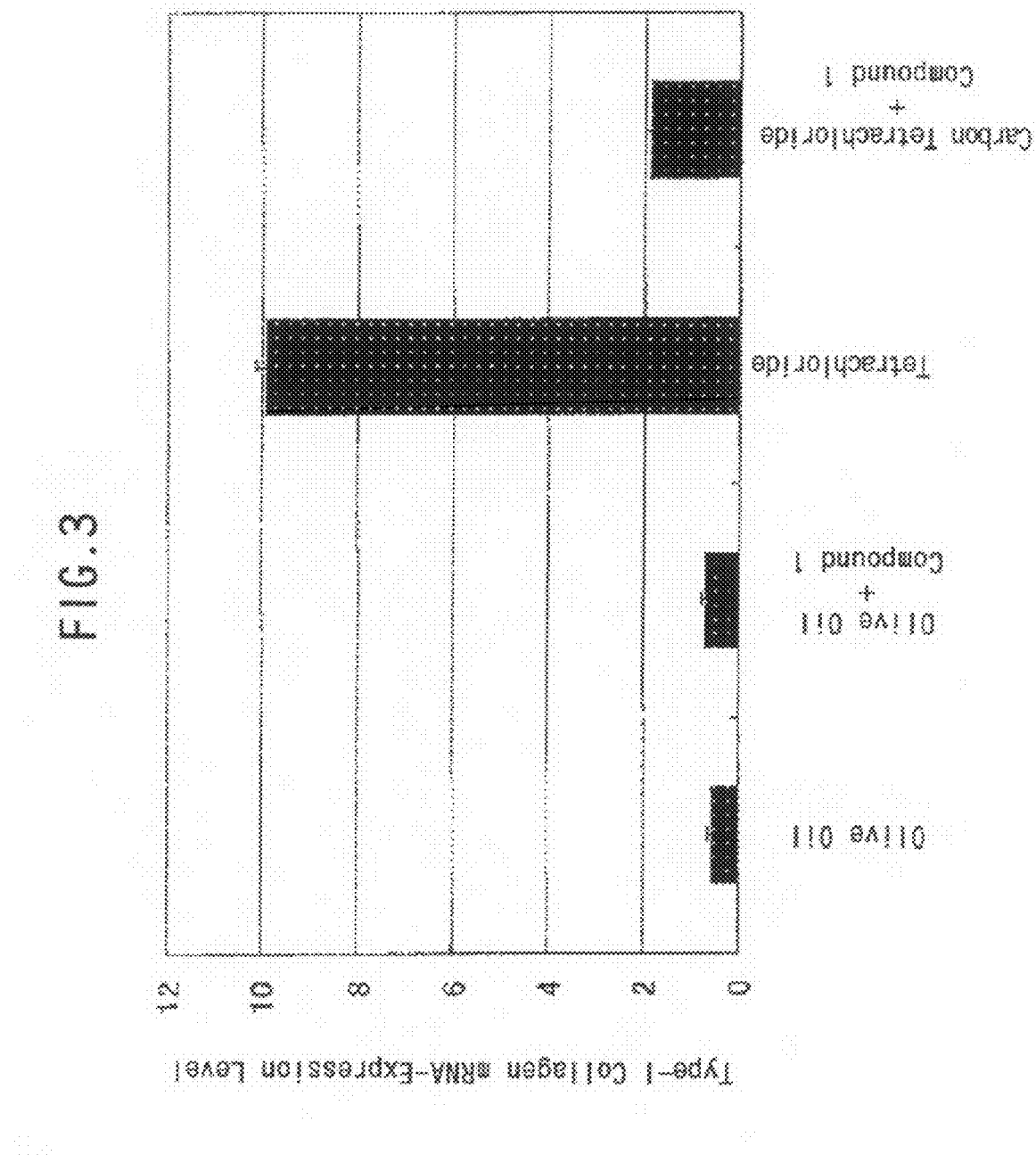
FIG. 3 is a diagram showing the action of the compound 1 relative to a type-I collagen mRNA-expression level in the liver.
Figure 4:
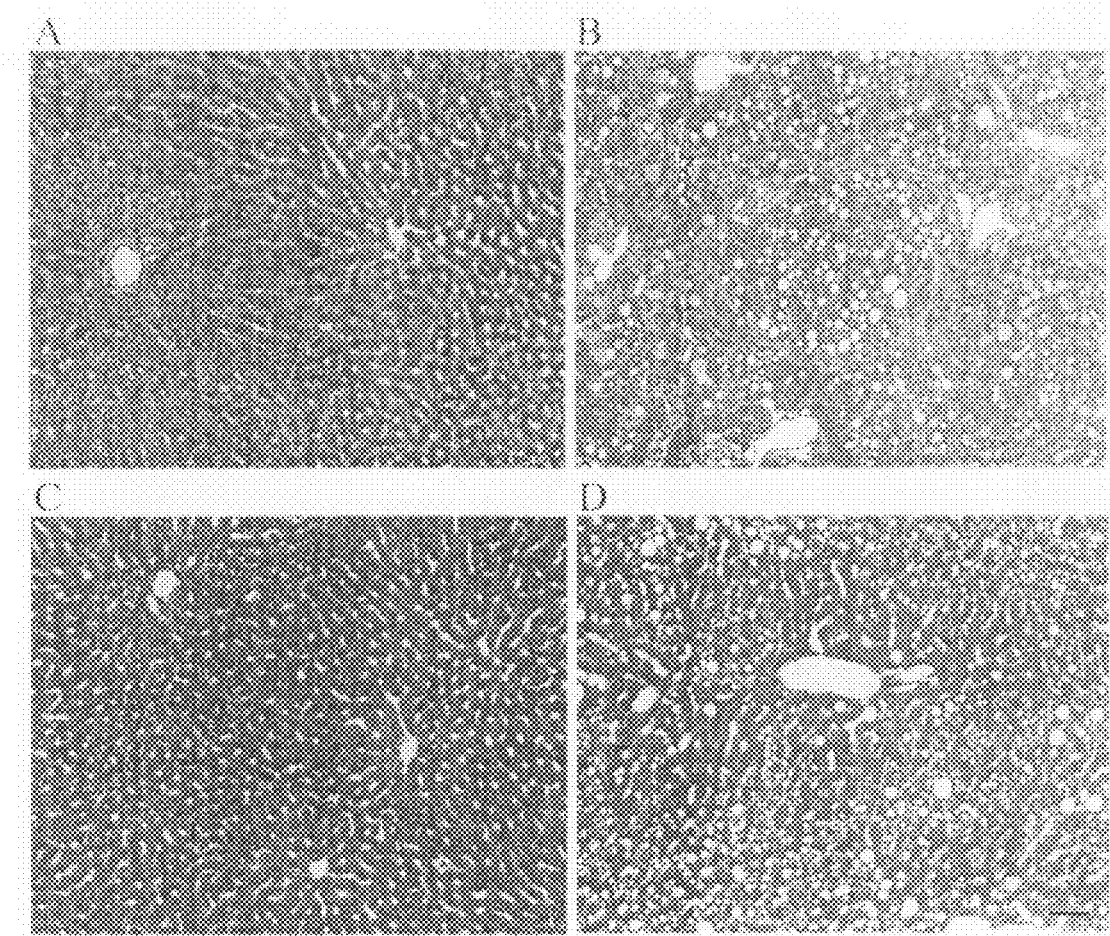
FIG. 4 is a diagram showing the state of lessening the accumulation of fibrous tissues by virtue of administration of the compound 1.
Figure 5:
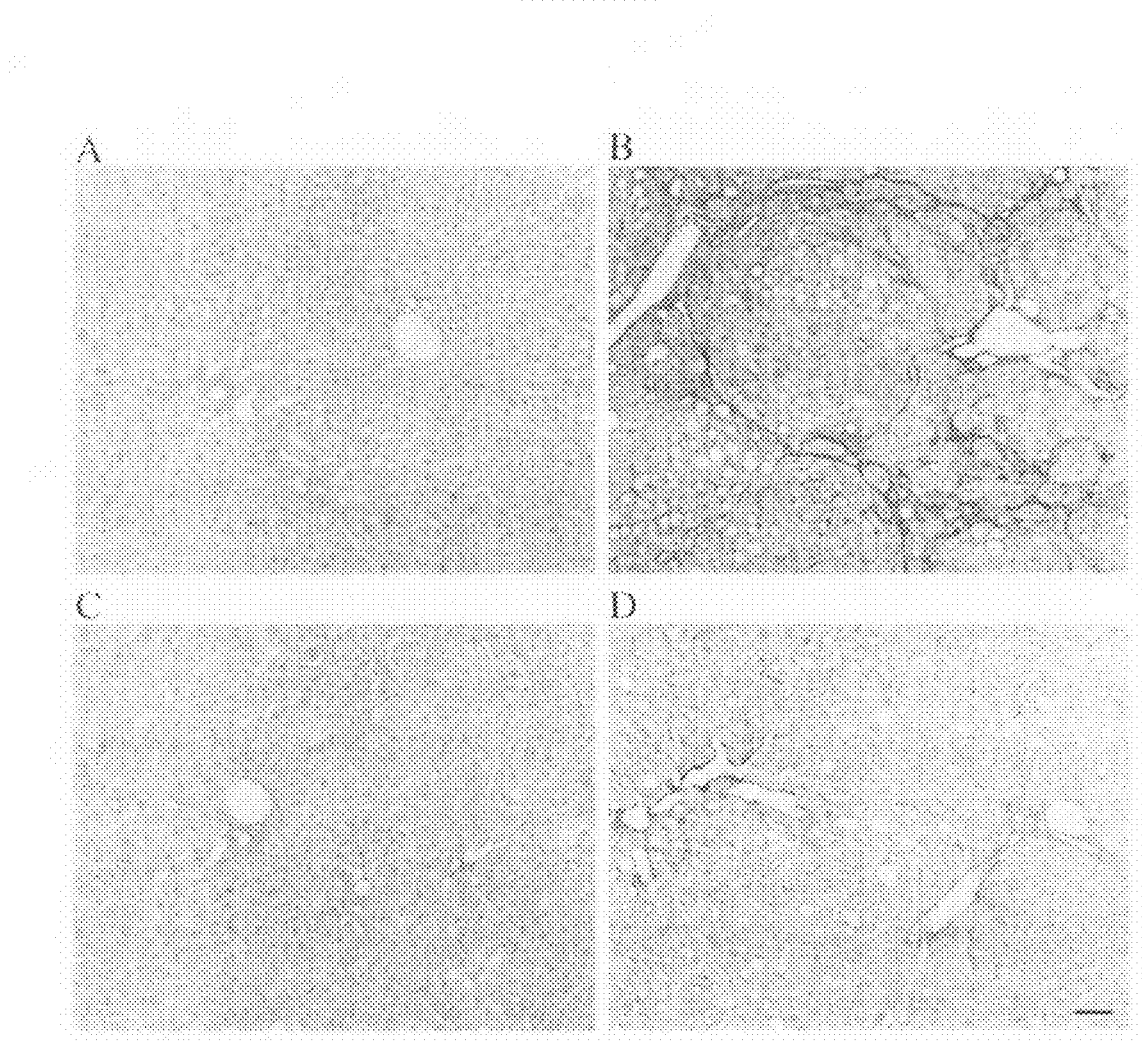
FIG. 5 is a diagram showing the state of suppressing the expression of TGF-β1 by virtue of administration of the compound 1.

The examination results of measurements of the blood AST, ALT, HA concentration are shown in Table 2. The examination results of measurements of the liver weight, spleen weight, and number of animals with ascites retention are shown in Table 3. The measurement results of the expression levels of TGF-$\beta$1 mRNA and type-I collagen mRNA are shown in FIG. 2 and FIG. 3. FIGS. 4 and 5 are photographs of hepatic tissues taken by using a Masson staining method and an immunohistochemical staining method (A: olive oil administration case, B: carbon tetrachloride administration case, C: olive oil-plus-compound 1 administration case, and D: carbon tetrachloride-plus-compound 1 administration case; and horizontal line on the bottom right: 100 μm).

TABLE 2

Effects on blood chemical examination values of rat models with carbon tetrachloride-induced liver cirrhosis

| Examination Item | Olive Oil | Olive Oil + Compound 1 | $CCl_4$ | $CCl_4$ + Compound 1 |
|---|---|---|---|---|
| AST (IU/L) | 195.7 ± 90.4 | 192.7 ± 93.4 | 2215.5 ± 110.2*** | 603.6 ± 126.3**+++ |
| ALT (IU/L) | 94.7 ± 35.1 | 93.7 ± 34.1 | 1418.3 ± 181.2*** | 422.4 ± 60.5**++ |
| ALB (g/dL) | 4.3 ± 0.1 | 4.3 ± 0.1 | 3.1 ± 0.1** | 3.8 ± 0.2*+ |
| T-Bil (mg/dL) | 0 | 0 | 0.34 ± 0.05* | 0.03 ± 0.02+ |
| HA (ng/mL) | 131.0 ± 19.5 | 136.7 ± 16.6 | 453.0 ± 19.7** | 237.7 ± 36.6*+ |

Compound 1: 2,3,5-trimethyl hydroquinone-1-hexylether
Value: Average value ± Standard deviation (n = 10)
p < 0.01 *P < 0.001 (Compared with olive oil administration group or olive oil-plus-compound 1 administration group)
+P < 0.05 ++<0.01 (Compared with $CCl_4$ administration group)

TABLE 3

Effects on body weight, hepatic, weight, pancreatic weight, and ascitic amount of rat models with carbon tetrachloride-induced liver cirrhosis

| Examination Item | Olive Oil | Olive Oil + Compound 1 | $CCl_4$ | $CCl_4$ + Compound 1 |
|---|---|---|---|---|
| Body weight (g) | 358.3 ± 6.1 | 361.5 ± 1.5 | 226.5 ± 7.9** | 240.8 ± 8.7* |
| Hepatic relative weight | 14.4 ± 1.6 | 14.8 ± 1.5 | 10.9 ± 2.1* | 16.1 ± 1.8+ |
| Pancreatic relative weight | 0.20 ± 0.01 | 0.20 ± 0.01 | 0.38 ± 0.06* | 0.28 ± 0.01+ |
| Number of animals with ascites retention | 0 | 0 | 8 | 1 |

Compound 1: 2,3,5-trimethyl hydroquinone-1-hexylether
Value: Average value ± Standard deviation (n = 10)
Hepatic and pancreatic relative weight: g (per 100 grams of body weight)
*p < 0.05 ***P < 0.001 (Compared with olive oil administration group or olive oil-plus-compound 1 administration group)
+P < 0.05 (Compared with $CCl_4$ administration group)

The experimental results shown in Tables 2 and 3 and FIGS. 2 and 3 show that the compound 1 of the invention has the function of suppressing increase in AST, ALT and hyaluronan concentration due to administration of carbon tetrachloride and increase in TGF-β1 mRNA-expression level and type-I collagen mRNA-expression level. The experimental results of the histopathologic inspection shown in FIGS. 4 and 5 confirmed that the accumulation of fibrous tissue and the expression of TGF-β1 can be suppressed by administration of the compound 1.

From the fact that administration to the olive oil-plus-compound 1 administration group showed no appreciable abnormality in each of the experimental Examples 1 and 2, it is evident that the compound 1 of the invention has a high level of security and is extremely useful as the hepatic fibrosis inhibitor.

While the present invention has been shown and described with reference to particular embodiments thereof, those skilled in the art will understand that other variations in form and detail may be made without departing from the scope and spirit of the invention.

What is claimed is:

1. A method of treating a patient having hepatic fibrosis, which comprises administering a therapeutically effective amount of a compound represented by Formula (1) to the patient:

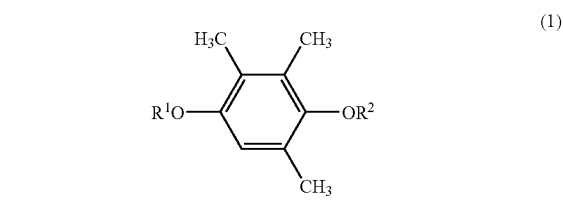

wherein $R^1$ represents an alkyl group with a carbon number of 4 to 8, and $R^2$ represents a hydrogen atom, alkylcarbonyl group with a carbon number of 2 to 6, or alkoxycarbonyl group with a carbon number of 2 to 6, and wherein the compound inhibits the expression of naofen.

2. The method set forth in claim 1, wherein said compound represented by said chemical formula (1) is 2,3,5-trimethyl hydroquinone-1-hexylether or 2,3,5-trimethyl hydroquinone-1-hexylether 4-acetate.

* * * * *